US00PP32537P2

(12) United States Plant Patent
Traven

(10) Patent No.: US PP32,537 P2
(45) Date of Patent: Dec. 1, 2020

(54) ***FICUS* PLANT NAMED 'PT-DF-14'**

(50) Latin Name: *Ficus carica*
Varietal Denomination: PT-DF-14

(71) Applicant: Lloyd R. Traven, Kintnersville, PA (US)

(72) Inventor: Lloyd R. Traven, Kintnersville, PA (US)

(73) Assignee: B&S PLANTS, LLC, Kintnersville, PA (US)

( * ) Notice: Subject to any disclaimer, the term of this patent is extended or adjusted under 35 U.S.C. 154(b) by 0 days.

(21) Appl. No.: 16/602,232

(22) Filed: Aug. 30, 2019

(51) Int. Cl.
*A01H 5/08* (2018.01)
*A01H 6/00* (2018.01)

(52) U.S. Cl.
USPC ..... Plt./211

(58) Field of Classification Search
USPC ..... Plt./211
CPC ... A01H 5/08; A01H 5/00; A01H 5/12; A01H 6/00
See application file for complete search history.

*Primary Examiner* — June Hwu
(74) *Attorney, Agent, or Firm* — Penny J. Aguirre

(57) ABSTRACT

A new cultivar of *Ficus carica* plant named 'PT-DF-14' that is characterized by its compact, very dwarf, and semi-upright and mounded plant habit, its prolific production of fruit that is present at all branch nodes, its fruit production that commencing very early; as soon as dormancy breaks, and continues to produce fruit until dormancy or year around if plants do not go dormant, and its good performance as a container plant due to its size.

2 Drawing Sheets

Botanical classification: *Ficus carica.*
Variety denomination: 'PT-DF-14'.

BACKGROUND OF THE INVENTION

The present invention relates to a new and distinct cultivar of *Ficus carica*. The new *Ficus* will hereafter be referred to by its cultivar name, 'PT-DF-14'. 'PT-DF-14' is a new cultivar of deciduous shrub grown for use as an ornamental and fruit bearing plant suitable for growing in containers.

The Inventor discovered the new cultivar in September of 2010 as a naturally occurring branch mutation of *Ficus* 'Chicago Hardy' (not patented) that was growing in a container in a production block in Kintnersville, Pa.

Asexual propagation of the new cultivar was first accomplished by stem cuttings by the Inventor in May of 2014 in Kintnersville, Pa. Asexual propagation by stem cuttings, tissue culture arid layering has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PT-DF-14' as a unique cultivar of *Ficus*.

1. 'PT-DF-14' exhibits a compact, very dwarf, and semi-upright and mounded plant habit.
2. 'PT-DF-14' exhibits prolific production of fruit that is present at all branch nodes.
3. 'PT-DF-14' exhibits fruit production that commencing very early; as soon as dormancy breaks, and continues to produce fruit until dormancy or year around if plants do not go dormant.
4. 'PT-DF-14' exhibits good performance as a container plant due to its size.

'Chicago Hardy', the parent of 'PT-DF-14', differs from 'PT-DF-14' in having a much larger plant size, in producing fruits in late summer that ripen very late in fall (often not before frost), in having longer branch internode lengths, and a more open upright plant habit. 'PT-DF-14' can be most closely compared to the *Ficus* cultivars 'Little Miss Figgy' (U.S. Plant Pat. No. 27,929) and 'Beer's Black' (not patented). 'Little Miss Figgy' differs from 'PT-DF-14' in having a much larger plant height, in producing much fewer fruits that ripen at the end of the season, and in having a more open and more upright plant habit. 'Beer's Black' differs from 'PT-DF-14' in being a small tree with a much larger plant height, and in producing fruit in one flush late in the season.

BRIEF DESCRIPTION OF THE DRAWINGS

The accompanying colored photographs illustrate the overall appearance and distinct characteristics of the new cultivar. The plant in the photograph is three years in age as grown outdoors in a 3-gallon container in Kintnersville, Pa.

The photograph in FIG. 1 provides a side view of the plant habit of 'PT-DF-14'.

Figure 1:
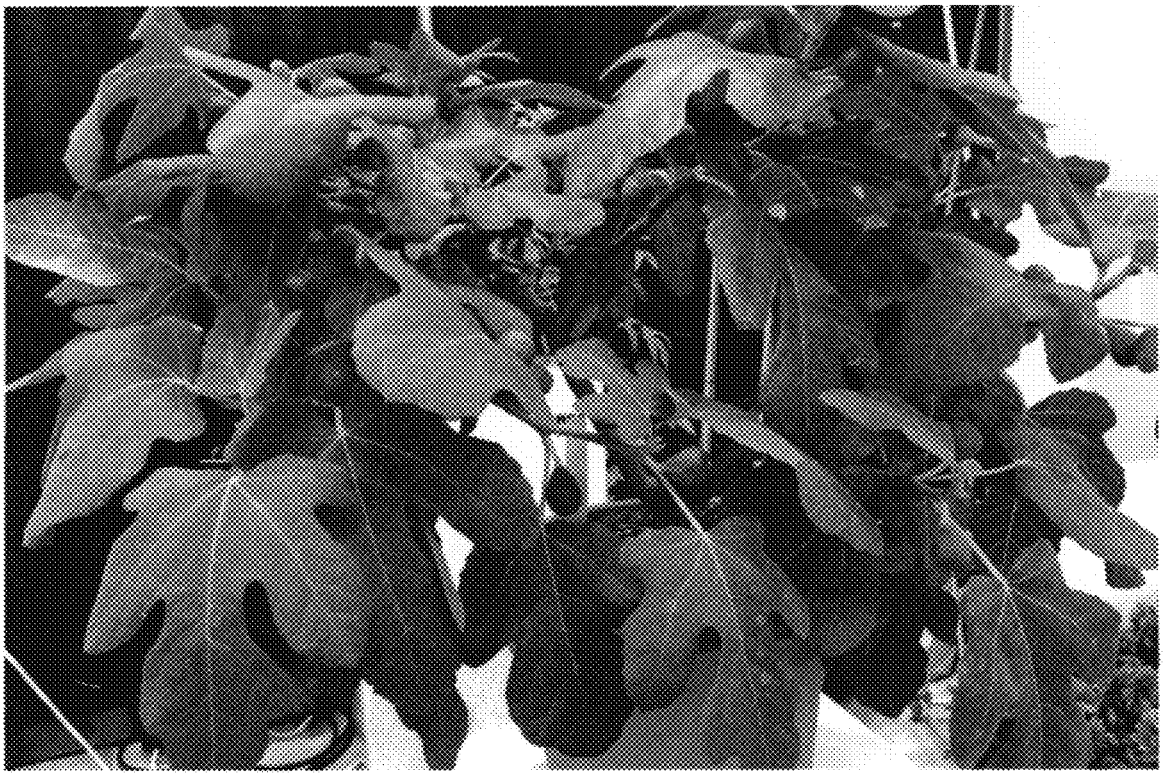
Figure 2:
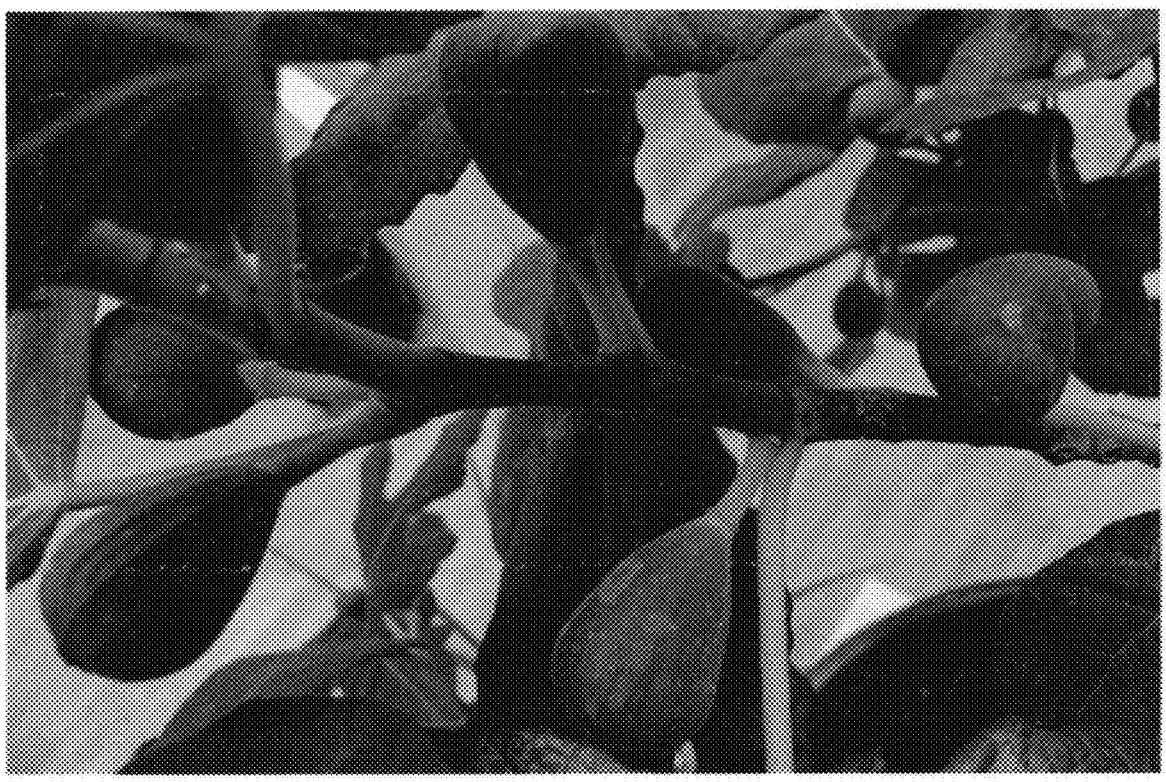

The photograph in FIG. 2 provides a close-up view of a stem with immature fruit of 'PT-DF-14'.

Figure 3:
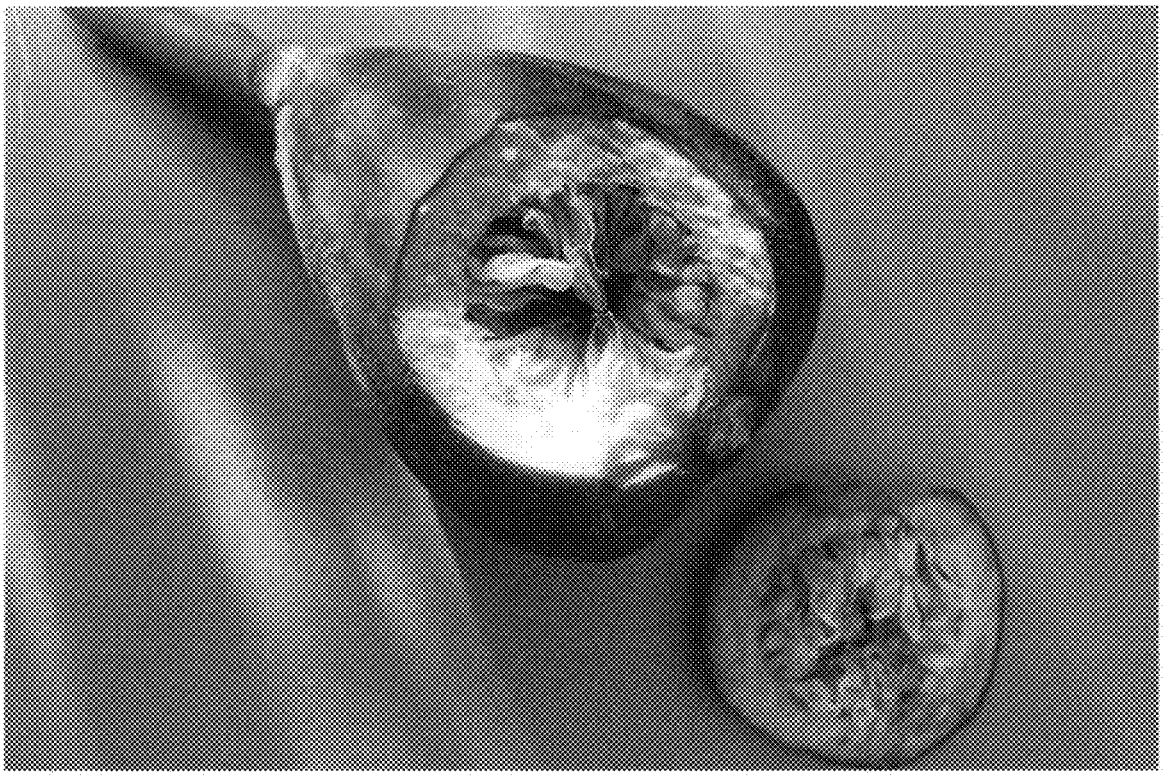

The photograph in FIG. 3 provides a close-up view of the interior of the infructescence of 'PT-DF-14'.

The colors in the photographs are as close as possible with the digital photography techniques available, the color values cited in the detailed botanical description accurately describe the colors of the new *Ficus*.

DETAILED BOTANICAL DESCRIPTION

The following is a detailed description of three-year-old plants of the new cultivar as grown outdoors in 3-gallon containers in Kintnersville, Pa. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Perennial shrub.

*Plant habit*.—Compact, very dwarf, semi-upright.

*Plant size*.—Reaches 60 to 76 cm in height and spread as a three-year-old plant grown in a 3-gallon container.

*Cold hardiness*.—At least in U.S.D.A. Zones 6.

*Diseases and pests*.—No susceptibility and resistance to diseases or pests has been observed.

*Root description*.—Fine and fibrous.

*Propagation*.—Stem cuttings, tissue culture (preferred) and layering.

*Growth rate*.—Slow.

*Root development*.—6 to 8 weeks to initiate roots and about 12 weeks to fully root as a young plant.

Stem description:

*Shape*.—Rounded.

*Stem color*.—Young branches; 145B and flushed with 200C as they mature, mature branches; 200C.

*Stem size*.—An average of 45 cm in length and 5 mm in diameter.

*Stem surface*.—Slightly glossy and moderately puberulent.

*Stem strength*.—Strong.

*Branching*.—An average of 6 lateral branches, plant does not form suckers or bark tubers or weeping secondary shoots, densely branched.

*Branch internodes*.—One-year-old shoots; an average of 2.5 cm in length, (short) and medium in number.

*Terminal buds*.—Triangular in shape with acuminate apex, 145B in color, an average of 1 cm in length and 7 mm in width at the base.

2-*year-old shoots*.—Straight in aspect with bud support swelling small.

Foliage description:

*Leaf shape*.—Cordate.

*Leaf division*.—Single.

*Leaf base*.—Hastate to truncate.

*Leaf apex*.—Bluntly acute to acute.

*Leaf venation*.—Pinnate, upper surface 142A, lower surface 142D, both sides densely covered in short stiff hairs that match surfaces.

*Leaf margins*.—Predominately 5 lobed, deeply lobed with central lobe lyrate and side lobes primarily oblanceolate in shape, an average of 5 cm in depth on a mature leaf, densely covered with short stiff hairs; an average of 0.5 mm in length and NN155A in color, no basal lateral lobes are present on the petiole sinus.

*Leaf arrangement*.—Alternate.

*Leaf attachment*.—Petiolate.

*Leaf surface*.—Upper surface rugose, rough to the touch and matte, lower surface matte, soft to the touch and very densely covered with minute, soft pubescence matching leaf surface color.

*Leaf fragrance*.—None.

*Leaf size*.—An average of 15.5 cm in length and 14 cm in width.

*Leaf quantity*.—An average of 4 per branch 45 cm in length.

*Leaf color*.—Young and mature upper surface; NN137A, young and mature lower surface; 137B.

*Petioles*.—An average of 4 cm in length and 3 mm in width and 142D in color, rounded in shape, surface is matte and densely covered with short hairs that match surface color and are 0.5 mm in length.

Flower and fruit description:

*Blooming period*.—Flowers develop internally in fruit as an infructescence, which are present from dormancy break in spring until fall or year around if dormancy is not present, fruit characteristics are similar through the season, fruit described are first crop produced from overwintering buds.

*Inflorescence type*.—Syconium, flowers borne internally on a hollow inverted receptacle, which is lined with numerous unisexual flowers, the flower itself is not visible as it blooms inside the infructescence.

*Lastingness of inflorescence*.—Not applicable, develops in fruit.

*Flower number*.—Numerous unisexual flowers per infructescence.

*Peduncle* (*fruit stalk*).—Round in shape, held outward from the main stem, an average of 1.5 cm in length and 3 mm in width, 142D in color, surface is matte and very densely covered with minute hairs matching surface color, easily abscisses from branch.

*Reproductive organs*.—Too minute to observe, senesce as fruit matures.

*Infructescence*.—Present at all axils of leaf nodes of branches and present soon after dormancy break until fall (or year around if no dormancy), obovate in shape, an average of 4 cm in length and 2 cm in diameter, rounded to flattened apex, fruit neck is absent, ostiole; an average of 1.3 mm in width, drop at the eye is absent, ostiole scales; adhered, an average of 2 mm in length and 1 mm in width, and 144C in color, resistant to ostiole end cracks, skin; firm and satiny, strong scratch resistance, attachment to skin is medium, moderately lenticillate with large lenticels 0.5 mm in length and 142D in color, longitudinal ribs, and skin cracks are absent, skin is difficult to peel adhering to about 95% or more of meat, fruit size and formation is uniform, outer surface color; NN137A when immature and becomes flushed with 187A to 187B at maturity, inner surface; 142D in color, fruit flesh is an average of 3 mm in thickness at the center, pulp; fleshy, neutral flavor, a blend of NN155B and 67A and 68C in color, firm, fruit cavity; 1 cm in width, 2 cm in length, fruitlets; not observed, seeds: numerous, 1 mm in diameter and 158A in color.

*Production type*.—Unifera.

*Abnormal fruit amount*.—Few.

*Fertility*.—Self-fertile.

*Fruit juiciness*.—Medium.

*Fruit use*.—Fruit is for use by home gardeners and not for commercial fruit production, therefore fruit chemistry and yield parameters have not been recorded.

It is claimed:

1. A new and distinct cultivar of *Ficus* plant named 'PT-DF-14' as herein illustrated and described.

* * * * *